(12) United States Patent
Swank

(10) Patent No.: US 7,459,133 B2
(45) Date of Patent: Dec. 2, 2008

(54) SYSTEM FOR AUTOMATIC/CONTINUOUS STERILIZATION OF PACKAGING MACHINE COMPONENTS

(75) Inventor: Ronald Swank, Woodstock, IL (US)

(73) Assignee: Tetra Laval Holdings & Finance, SA, Pully (CH)

(*) Notice: Subject to any disclaimer, the term of this patent is extended or adjusted under 35 U.S.C. 154(b) by 781 days.

(21) Appl. No.: 10/400,305

(22) Filed: Mar. 27, 2003

(65) Prior Publication Data
US 2004/0191115 A1 Sep. 30, 2004

(51) Int. Cl.
*A61L 2/00* (2006.01)
*B65B 55/00* (2006.01)
(52) U.S. Cl. .................. 422/292; 422/1; 53/167
(58) Field of Classification Search .......... 422/280, 422/292; 53/167
See application file for complete search history.

(56) References Cited

U.S. PATENT DOCUMENTS

| | | | |
|---|---|---|---|
| 2,697,313 A | 12/1954 | Wilcox | |
| 3,187,646 A * | 6/1965 | Monroe et al. | 493/164 |
| 3,466,841 A | 9/1969 | Rausing | |
| 3,513,627 A | 5/1970 | Doucette et al. | |
| 3,681,892 A | 8/1972 | Safranski | |
| 3,820,300 A | 6/1974 | Reinecke et al. | |
| 4,175,140 A | 11/1979 | Bachman et al. | |
| 4,225,556 A | 9/1980 | Löthmann et al. | |
| 4,233,271 A | 11/1980 | Ernstsson et al. | |
| 4,289,728 A | 9/1981 | Peel et al. | |
| 4,537,007 A | 8/1985 | Lattanzi | |
| 4,566,251 A | 1/1986 | Spisak et al. | |
| 4,590,734 A * | 5/1986 | Ueda | 53/52 |
| 4,590,740 A | 5/1986 | Rodocker | |
| 4,683,701 A | 8/1987 | Rangwala et al. | |
| 4,963,335 A | 10/1990 | Adachi et al. | |
| 4,992,247 A * | 2/1991 | Foti | 422/304 |
| 5,011,664 A | 4/1991 | Olanders | |
| 5,053,196 A * | 10/1991 | Ide et al. | 422/28 |
| 5,069,017 A | 12/1991 | Fabricius | |
| 5,114,670 A | 5/1992 | Duffey | |
| 5,114,671 A | 5/1992 | Olanders | |
| 5,122,340 A | 6/1992 | Shimamura et al. | |
| 5,135,714 A | 8/1992 | Wang | |
| 5,262,126 A | 11/1993 | Shimamura et al. | |
| 5,356,592 A | 10/1994 | Balla et al. | |
| 5,368,828 A | 11/1994 | Carlson | |
| 5,424,034 A | 6/1995 | Hilmersson | |
| 5,569,438 A | 10/1996 | Hilmersson | |
| 5,587,127 A | 12/1996 | Carlson | |
| 5,639,432 A | 6/1997 | Carlson | |

(Continued)

*Primary Examiner*—Jill Warden
*Assistant Examiner*—Kevin C Joyner
(74) *Attorney, Agent, or Firm*—Levenfeld Pearlstein, LLC

(57) ABSTRACT

An automatic, continuous sterilization system is for use in a form, fill and seal packaging machine for forming, filling and sealing packages. The machine has a turret carrying a plurality of mandrels on which the packages are carried. A bottom panel heating station has a reciprocating bottom panel heater. The sterilization system includes a sterilant source for supplying a sterilant and a sterilant inlet at the bottom panel heater. Packages are positioned on one of the plurality of mandrels and are indexed to the bottom panel heater. The sterilant is introduced to the mandrel when the carton is positioned thereon. Introduction of the sterilant provides a log reduction of microbial colony forming units of at least about 5.9 after ten minutes of machine operation. A method for continuous mandrel sterilization is also disclosed.

8 Claims, 4 Drawing Sheets

U.S. PATENT DOCUMENTS

| | | |
|---|---|---|
| 5,809,739 A | 9/1998 | Eno |
| 5,809,740 A | 9/1998 | Sundby et al. |
| 6,056,918 A | 5/2000 | Palaniappan et al. |
| 6,058,678 A | 5/2000 | Lees |
| 6,066,081 A | 5/2000 | Bachner |
| 6,085,496 A | 7/2000 | Fontanazzi et al. |
| 6,101,786 A | 8/2000 | Lees |
| 6,120,730 A * | 9/2000 | Palaniappan et al. .......... 422/28 |
| 6,406,666 B1 | 6/2002 | Cicha et al. |
| 6,752,959 B2 * | 6/2004 | Smith et al. .................... 422/28 |
| 7,008,592 B2 * | 3/2006 | Sias et al. ..................... 422/28 |

* cited by examiner

SYSTEM FOR AUTOMATIC/CONTINUOUS STERILIZATION OF PACKAGING MACHINE COMPONENTS

BACKGROUND OF THE INVENTION

The present invention is directed to a system for sterilizing components such as mandrels in a packaging machine. More particularly, the present invention is directed to an automatic, continuous sterilization system for form, fill and seal packaging machines.

Form, fill and seal packaging machine are well known in the art, as are sterilization systems for use with such machines. These machines are widely used in the food packaging industry for forming a package, filling the package with a liquid or solid food (or a mixture of liquid and solid foods), and sealing the package after filling.

In such machines, sterilization systems are in place to eradicate (i.e., kill) microbes such as bacteria, yeast and mold. Commonly, the sterilization systems are directed to sterilizing the packages before and/or after forming the package, prior to filling and sealing.

Different types of sterilization systems are also used. For example, one type of sterilization system uses hydrogen peroxide as a liquid or in vapor form that is sprayed onto the exterior of the packages and/or into the interior of the packages. Other types of sterilization systems use energy in the form of, for example, ultraviolet emissions or electron beam emissions to kill these microbes. Still other types of sterilization systems use combinations of these systems and methods.

Nevertheless, prevailing sterilization systems use hydrogen peroxide that is applied directly to the packaging. The hydrogen peroxide sterilant can be applied in a sterilization station within the machine, or it can be pre-applied at a location prior to the machine proper. Exemplary arrangements for machines and machine sterilizations systems, methods and the like are disclosed in Cicha, et al., U.S. Pat. No. 6,406,666, Palaniappan, et al., U.S. Pat. No. 6,120,730, Lees, U.S. Pat. No. 6,058,678, Palaniappan, et al., U.S. Pat. No. 6,056,918 and Eno, U.S. Pat. No. 5,809,740, all of which patents are commonly assigned with the present application and are incorporated herein by reference.

Although all of these systems work well and function well, there are limits to the amount of residual hydrogen peroxide (which is generally present in the form of condensed vapor remaining on the packaging material surface) that can remain on packaging when food is introduced to the package. As such an appropriate drying time is necessary to assure that these upper limits are met.

Moreover, it is conventionally believed that microbes present in the packaging can result from contact of the packaging with portions or elements or parts of the machine. One such part, in a machine that forms, fills and seals gable-top packages or cartons, is the carton mandrel. The mandrel is that machine element around which the carton is formed (the carton is inserted onto the mandrel), for folding and sealing the carton bottom panels. Typically, the mandrels are positioned on a rotating turret and, in an indexed manner, receive cartons opened into a tubular form at a station, index the cartons to a subsequent station for pre-folding, index the cartons to another station to heat the carton panels, fold the panels into a desired pattern or orientation and "press" the heated panels on the mandrel to form the sealed cartons bottom all.

In that there are a considerable number of machine elements that contact the carton (and in particular the mandrels that contact carton interior surfaces) in this "forming" process, it is necessary to carry out sterilization following these cartons forming steps. As such, sterilization stations or tunnels are positioned on a typical machine following the forming stations.

Furthermore, it is also necessary to periodically clean, sanitize and/or sterilize the mandrels. Presently, mandrel cleaning, sanitizing or sterilizing is accomplished by stopping the package forming and filling operations and manually or automatically cleaning, sanitizing and/or sterilizing the mandrel surfaces. Ceasing the package forming and filling functions for manual or automatic cleaning of the mandrels reduces the machine efficiency and adds labor costs to overall machine operations.

In addition, manual sanitizing procedures are extremely variable due to various operator techniques and the level of operator skill and training. Manual procedures are difficult to monitor and as such make it difficult to control the consistency or efficacy of the sterilization process. Further, many manual and automatic procedures which require that production be stopped for sterilization employ sanitizers or sterilants that are liquid based and require a drying step which further reduces machine efficiency. Examples of water based products are alcohols and quats which need to dry before commencing production. If production is allowed to start prior to the machine surfaces being fully dried, the very steps that are intended to reduce contamination can contribute to further contamination and subsequent package spoilage. Additionally, these known methods are not continuous or automatic operations that can be accomplished without stopping production activities.

Furthermore, more than just meeting the sterility or cleanliness standards (which permit some amount of microbes), it is known that greater amounts of microbial contamination will result in packaged foods that have shorter shelf lives. That is, typically, as the amount of microbial contamination increases, the shelf life of the product decreases. This is of greatest concern for long or extended shelf life products and for aseptic products where the product must meet strict commercial sterility requirements. For all hygiene levels, these requirements are strictly controlled and enforced by governmental regulatory agencies such as for example the United States Food and Drug Administration (USFDA) and the United States Department of Agriculture (USDA).

It has been found that during package forming operations, mandrels are exposed to environmental factors such as dust, paper particles, plastic particles and humidity. All of these environmental factors serve to increase the microbial load on the mandrel surfaces and subsequent contamination of the interior product surfaces of the package.

It has also been observed that although microbial loading on the mandrel surfaces is generally low at the start of production, the microbial load increase over time. Thus, the contamination and spoilage microorganisms delivered to the packages will increase over time. In addition, microbial contamination in the form of condensate, water drops or other particulate forms (which are generally highly contaminated), are also readily transferred to interior product contact package surfaces.

Accordingly, there exists a need for a sterilization system for a form, fill and seal packaging machine that increases the ability to kill or otherwise eliminate microbes that may be present within the machine or on the packaging. Desirably, such a sterilization system is compatible with the overall operation of known form, fill and seal machines, and operates automatically, on a continuous basis without interruption to machine filling operations. Most desirably, such a system works in conjunction with and/or uses systems and subsystems already within the machines to provide this enhanced microbe eradication characteristic.

BRIEF SUMMARY OF THE INVENTION

A form, fill and seal packaging machine includes an automatic, continuous mandrel sterilization system. The machine has a turret carrying a plurality of mandrels on which the cartons are carried for partial carton erection. The machine includes a bottom panel heating station having a reciprocating bottom panel heater.

The sterilization system includes a sterilant source for supplying a sterilant and means for introducing a sterilant at the bottom panel heater. In one form, the means for introducing the sterilant includes a sterilant inlet at the bottom panel heater. Cartons are positioned on one of the mandrels and are indexed to the bottom panel heater. The sterilant is introduced to the mandrel through the heater when the carton is positioned at the heater, with the heater reciprocating into the carton. Introduction of the sterilant provides a log reduction of microbial colony forming units of at least 5.9 after ten minutes of machine operation when using hydrogen peroxide, at a concentration of about 35 percent, as the sterilant.

In a present sterilization system, the sterilant is vaporized at a sterilant vaporizer to inlet at the bottom panel heater. A preferred sterilant is vaporized hydrogen peroxide present in a concentration is less than or about 35 percent. Presently, hydrogen peroxide concentration is about 3 percent to about 35 percent.

In a preferred machine arrangement, the sterilant source is a common source for the form, fill and seal packaging machine. A nozzle or other, similar device, can be present at the sterilant inlet for introducing sterilant into the bottom panel heater or other container-contacting surfaces of the mandrel.

A method for sterilizing a mandrel in a form, fill and seal packaging machine includes the steps of operating the form, fill and seal packaging machine, positioning a carton having an open bottom formed from a plurality of flaps on a mandrel and rotating the mandrel having the carton thereon to a bottom heater. The method further includes the steps of providing a sterilant inlet at the bottom heater, indexing the bottom heater toward the carton open bottom and introducing a sterilant at the bottom heater.

Introducing the sterilant provides a log reduction of microbial colony forming units of at least 5.9 after ten minutes of machine operation. A preferred method includes vaporizing the sterilant prior to introducing the sterilant at the bottom heater.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
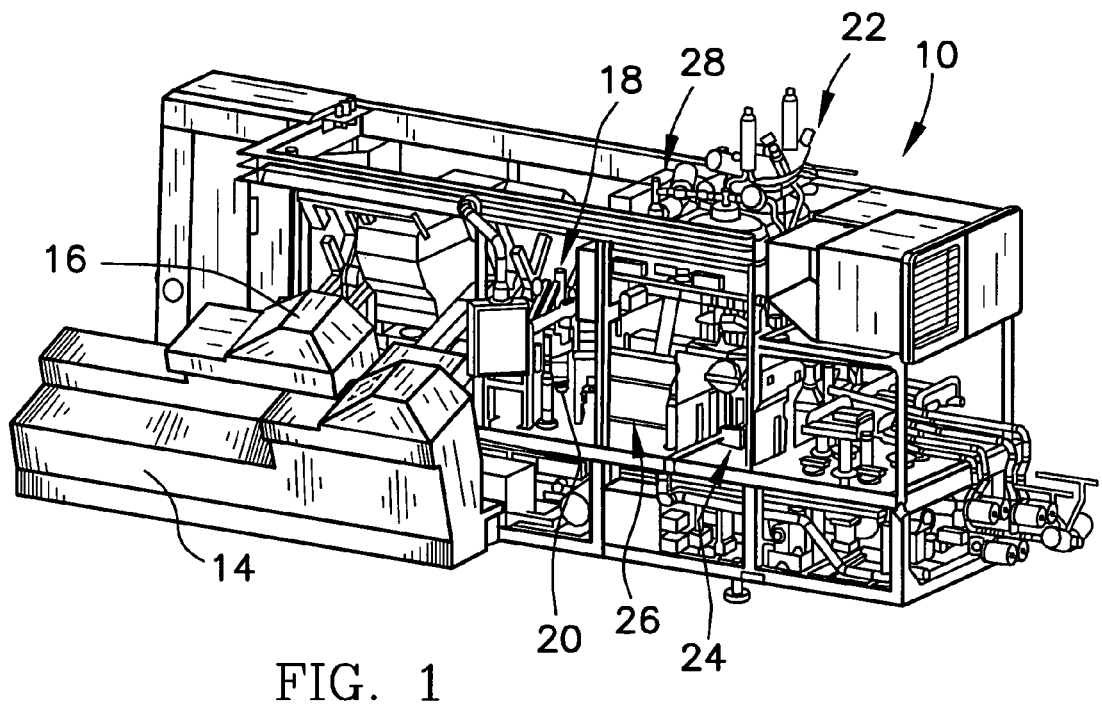
FIG. 1 illustrates an exemplary form, fill and seal packaging machine having an automatic, continuous mandrel sterilization system embodying the principles of the present invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Referring now to the figure and in particular to FIG. 1, there is shown a form, fill and seal packaging machine 10 that incorporates a system 12 for automatic/continuous sterilization of packaging machine mandrels, embodying the principles of the present invention. The form, fill and seal packaging machine 10 can be such as that disclosed in Katsumata, U.S. Pat. No. 6,012,267, which patent is assigned to the assignee of the present invention and is incorporated by reference herein. The machine 10 is configured to store, erect, fill and seal a series of cartons C moving therethrough.

A typical filling machine 10 includes a carton magazine 14 for storing the flat, folded carton blanks. The filling machine 10 includes a carton erection station 16 that receives the cartons in the flat, folded form, erects the cartons into a tubular form and seals the bottom flaps thereof. A fitment, such as the now widely recognized plastic spout (not shown), may then be applied to the partially erected carton.

The carton C can then be sterilized using, for example, vaporized hydrogen peroxide and/or ultraviolet radiation, and/or heat, at one or more sterilization stations 18. As will be recognized by those skilled in the art, sterilizing the cartons C reduces or eliminates the microbes such as bacteria- yeast and molds therein which increases the shelf life of the stored product. This is particularly true for liquid food products, such as milk, juice and the like. Exemplary sterilization systems are disclosed in Palaniappan et al., U.S. Pat. Nos. 6,120, 730 and 6,056,918, which patents are assigned to the assignee of the present invention and are incorporated by reference herein.

The partially erected carton C, which at this point has the bottom flaps folded and sealed to form a sealed carton bottom and optionally a fitment applied thereto, is then conveyed to a top panel pre-folding station 20. Subsequent to pre-folding, the partially erected carton C is filled with product at a filling station 22. As set forth above, this can be any one of a number of different types of product including, but not limited to, liquid food product, such as milk, juice or the like.

Following the filling operation, the top panels, at about the top fins, are heated to soften the polymeric coating on the packaging material for subsequent sealing. The carton C is then conveyed into a top sealing station 24 at which the top panels are folded toward one another and compressed at the top fin panels to form the top seal for the carton C. Subsequent to top sealing, the cartons C are conveyed out of the form, fill and seal packaging machine 10.

In a typical form, fill and seal packaging machine 10, the space or region, indicated generally at 26, from the sterilization station to the top sealing station is maintained as a sterile environment region. To this end, air is passed through an air sterilization system, indicated generally at 28, that can include a series of filters, such as high efficiency particulate adsorbing filters (HEPA filters), membrane filters, and the like, to remove particulates as well as microorganisms that may be in the air. The sterile environment within the region 26 of the machine 10 is maintained at a positive pressure relative to the outside environment. In this manner, any leakage is outward from the sterile machine 10 environment (as at 26), rather than into the machine environment (i.e., out-leakage rather than in-leakage). This facilitates maintaining this environment in a sterile condition.

In an effort to further reduce the presence of bacteria in the machine environment, in accordance with the present invention, the form, fill and seal packaging machine 10 includes an automatic, continuous sterilization system 12 that is configured for use with (i.e., for directly sterilizing) the mandrels 34 on which the carton C are carried for partial erection, that is folding the bottom panels and forming the bottom wall.

As will be recognized by those skilled in the art and from a study of the drawings, in the forming of the cartons, the unformed carton in tubular form is inserted onto the mandrel 34 at a first station or position 36. The mandrel 34 is then indexed to a position, indicated at 38, at which the bottom flaps F are pre-folded, heated, final-folded and subject to compression as by an anvil or pressure plate (not shown) that is urged against the bottom flaps F which are positioned on the bottom plate or cap 35 of the mandrel 34.

A heater 40, which moves into the open carton C bottom end, uses a stream of heated air (through conduit 41) to raise the temperature of the carton coating material to a predetermined temperature. This softens the coatings so that the coatings on the compressed flaps fuse into one another to form a liquid tight bottom wall seal.

In a current sterilization system 12, a sterilant is fed to the heaters 40 and is sprayed into the heaters 40. Although the term "sprayed" has been used, it will be appreciated by those skilled in the art that in a preferred operation the sterilant is vaporized, as by heating to a temperature above the boiling point, to produce a "dry" sterilant vapor. It has been found that the sterilant vapor provides a number of important benefits. First, the mandrels 34 are maintained in a more hygienic manner in that they are directly subjected to vaporized sterilant. As such, not only are the mandrels 34 on which the cartons C reside "cleaner", but it is believed that the cartons C themselves are less susceptible to microbial contamination because the sterilant vapor tends to migrate onto the carton C surfaces as well.

In order to properly operate in an environment in which a sterilant is sprayed into the heaters 40, it is necessary to assure that the sterilant does not condense onto the mandrels 34 or the carton C surfaces. As such, the mandrel surface temperature is preferably maintained at a temperature that precludes condensation. In conjunction with the elevated sterilant temperature, it has also been found to be advantageous to maintain the heaters 40 at a sufficiently elevated temperature to maintain the sterilant in a vapor phase, rather than allowing the vapor to condense.

In order to provide the maximum eradication effect, it has been found that it is advantageous to provide the vapor from the heaters 40 to the mandrels 34 when a carton C is positioned on each of the mandrels 34. It is believed that the carton C has a concentrating or focusing effect and directs the vapor onto the mandrel surfaces 34. Thus, a maximum amount of sterilant is directed onto the mandrel 34.

In a present sterilization system 12, the sterilant that is used is the same sterilant that is used in the overall form, fill and seal packaging machine 10, and is used in the same concentration as that used in the machine 10. In a present system 12, the sterilant is hydrogen peroxide and can be used in concentrations up to about 35 to about 50 percent, but more specifically at about 3 percent. Advantageously, using hydrogen peroxide at the same concentration as that used for "other" sterilization (e.g., carton sterilization) within the machine 10 precludes the need for a secondary sterilant supply system. That is, a single supply system can be used to provide sterilant for both the overall form, fill and seal machine 10 carton sterilization, as well as mandrel 34 sterilization. Those skilled in the art will recognize that the present sterilization system 12 can be used in conjunction with other, e.g., known, types of sterilizations systems within the machine 10. The hydrogen peroxide is vaporized at a common vapor generating system 39, such as that disclosed in Cicha, et al., U.S. Pat. No. 6,406,666 which patent is commonly assigned with the present application and is incorporated herein by reference.

Figure 2:
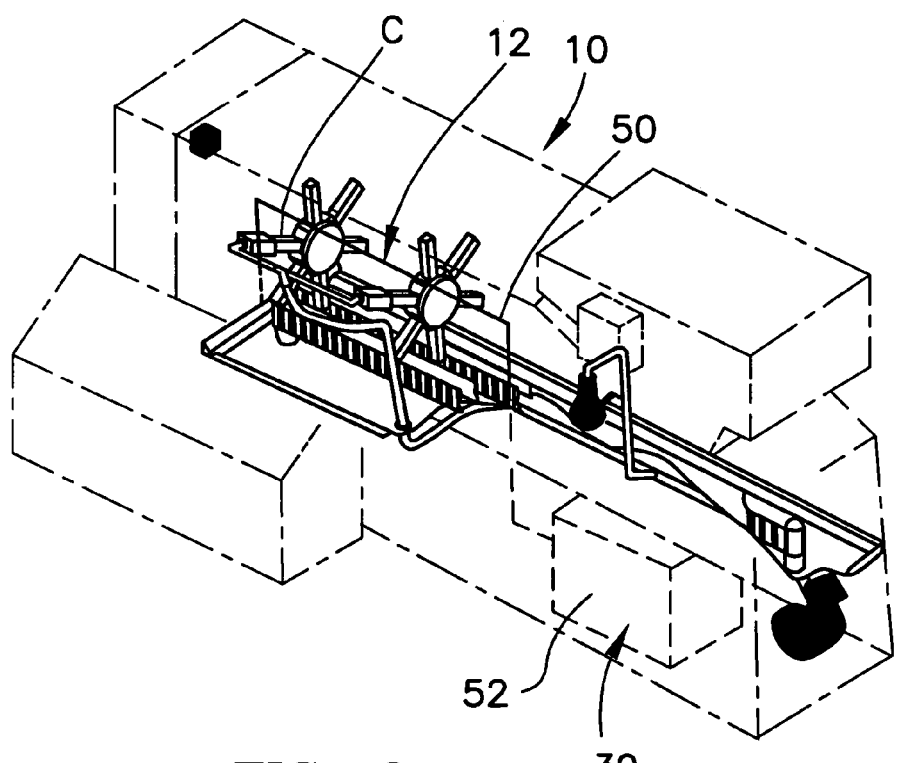
FIG. 2 is a schematic illustration of the sterilization system configured as part of the overall machine sterilization system.
Figure 3:
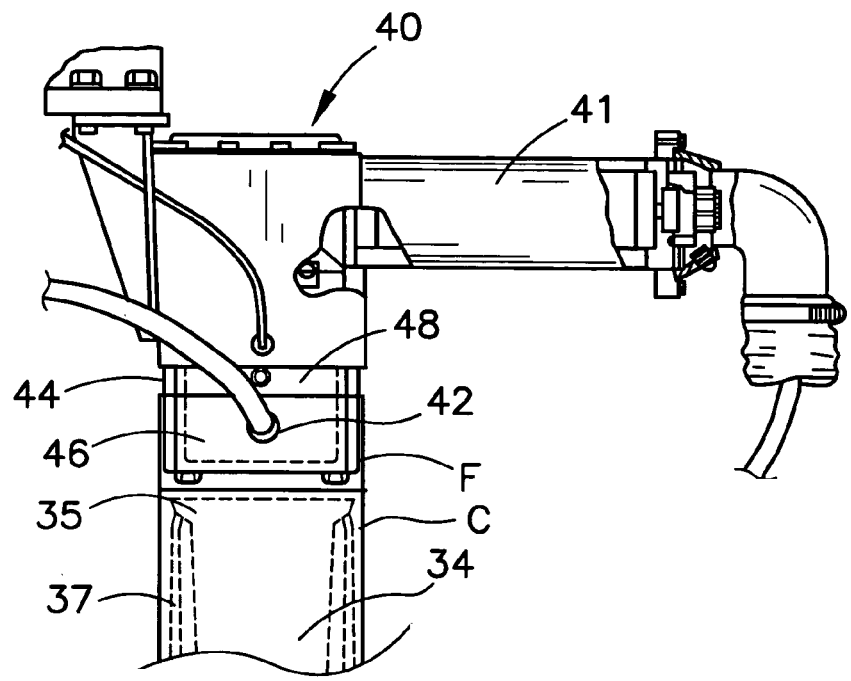
FIG. 3 is an illustration of a turret having a plurality of mandrels mounted thereto, and illustrating the present mandrel sterilization system.
Figure 4:
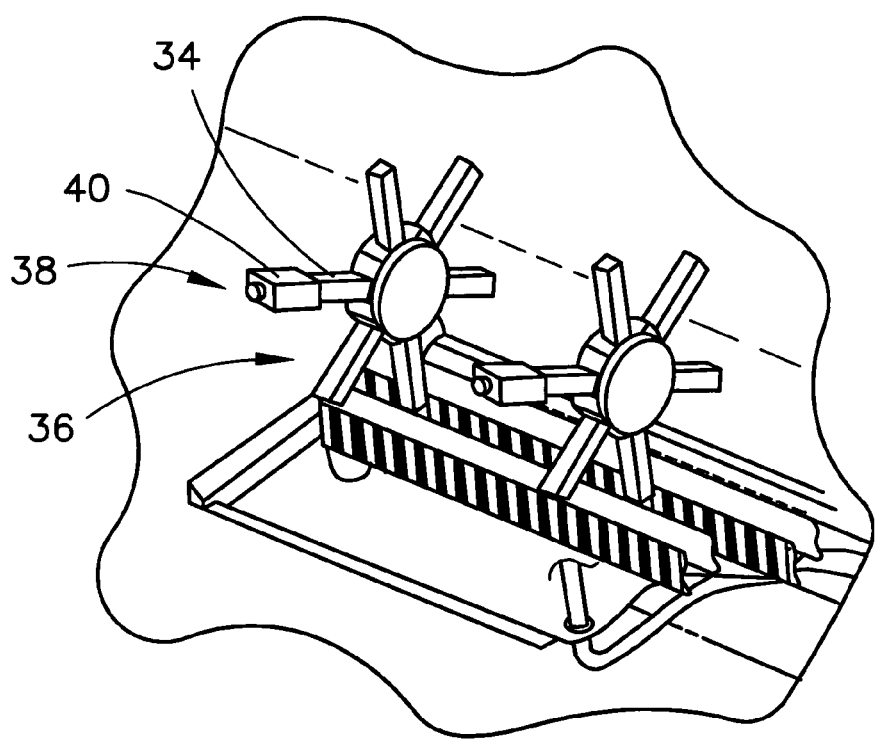
FIG. 4 is an illustration of the sterilant feed to the bottom flap heaters and the sterilant vapor injection nozzle location.

In a present machine 10, the hydrogen peroxide for mandrel 34 sterilization is introduced into the machine 10 at the bottom heaters 40, as the heater 40 is moved or indexed into the carton C. In this manner, as set forth above, the sterilant is directed to the mandrels 34 rather than merely distributed into the general area of the mandrels. A nozzle 42 is positioned in an outer wall or housing portion 44 of the heater. The nozzle 42 is configured to disperse the hydrogen peroxide into the area of the heater 40 proximate that portion of the heater 40 that is inserted into the end of the carton C (at the flaps F) for heating the bottom flaps F. The nozzle is positioned at about the heater air manifold 46. FIG. 3 illustrates a feed line 48 that is routed to the heater outer shell 44, and the relative positioning of the nozzle 42 along the heater 40. As seen in FIG. 2, which schematically shows the sterilant system 12, flow conduits 50 (e.g., piping and tubing) are routed from the sterilant supply 52 to the heater nozzles 42.

Studies were conducted to determine the microbial eradication on mandrels 34 that were subjected to vaporized sterilant introduced at the heaters 40. In each of studies noted below, the operating parameters that were used were a machine speed equivalent to 14,000 cartons per hour (when operating at "normal" operating speed), a hydrogen peroxide flow rate of 0.5 liters per hour, an air flow rate (for mixing with the hydrogen peroxide) of 84.0 liters per minute, and a hydrogen peroxide heater temperature of 185° C. The efficacy of the mandrel sterilization was studied for both the mandrel caps 35 and the mandrel side tubes 37 (see FIG. 3).

Each of the studies was further carried out using a testing media of *bacillus atrophaeus* spores for inoculating the mandrels. The mandrels were inoculated by spraying, using an aerating spray bottle having a solution with a concentration of about 7 log *bacillus* spores. The mandrels were then allowed to air dry. Controls were swabbed using cotton swabs to assure that the mandrels were properly inoculated. Following the machine operating period of the test, the mandrels were swabbed and the *bacillus* spores transferred to an agar media for incubation of the spores (at 32° C. for 48 hours) and subsequent recovery.

Six discrete tests were performed that included: (1) confirming mandrel inoculation and determining swab efficiency procedure; (2) evaluating microbial reduction on the mandrel caps due to rub-off (e.g., mechanical contact between the carton and mandrel cap), without sterilant application; (3) evaluating microbial reduction on the mandrel caps at varying hydrogen peroxide concentrations and at varying times with cartons running through the machine; (4) evaluating microbial reduction on the mandrel caps at a hydrogen peroxide concentration of 3.12 percent, at varying times, without cartons running through the machine; (5) evaluating microbial reduction on the mandrel caps and side tubes at a hydrogen peroxide concentration of 2.59 percent, at varying times, without cartons running through the machine and with the bottom heater indexed at a slow speed; and (6) evaluating microbial reduction on the mandrel caps and side tubes at a hydrogen peroxide concentration of 2.52 percent, at varying times, with cartons running through the machine.

In the tables that follow, colony forming unit is noted as CFU. CFU/mL is the count of colony forming units per milliliter of solution after swabbing and incubating. The columns noted as "Result #1 CFU/mL" and "Result #2 CFU/mL" in Tables 1, 2, 4, 5 and 6 are the raw count data. The columns noted as "Average CFU/mL" are, as noted above, count data of colony forming units per milliliter of solution measured after swabbing and incubation. The column noted as "Average CFU/mandrel" is calculated based upon the surface area of the mandrel. The column entitled "Log" is the logarithmic measure of the Average CFU/mandrel. In Table 6, the swab site is indicated as "C" for a swab of the mandrel cap and "T" for a swab of the mandrel tubes.

In Tables 2, 4, 5 and 6, the samples (swabs) were taken at different times to determine the efficacy over time of the sterilant vapor application. The times are shown in minutes in each of these tables.

Tables 3A and 3B show the microbial load (Table 3A) and reduction in microbial load (Table 3B) as a function of time and as a function of hydrogen peroxide concentration in the vapor. The time is shown in minutes and the percent H2O2 column indicates the concentration of hydrogen peroxide in the vapor. Table 3A shows the microbial load in CFU per mandrel and Table 3B and is the mathematical representation of the log reduction per mandrel.

TABLE 1

SWAB RECOVERY EFFICIENCY

| Sample # | Result #1 CFU/mL | Result #2 CFU/mL | Average CFU/mL | Average CFU/mandrel | Log |
|---|---|---|---|---|---|
| 1 | 3.10E+05 | 4.50E+05 | 3.80E+05 | 1.52E+06 | 6.18 |
| 2 | 6.70E+05 | 7.40E+05 | 7.05E+05 | 2.82E+06 | 6.45 |
| 3 | 2.60E+05 | 2.20E+05 | 2.40E+05 | 9.60E+05 | 5.98 |
| 4 | 4.30E+05 | 3.40E+05 | 3.85E+05 | 1.54E+06 | 6.19 |
| 5 | 2.80E+05 | 3.80E+05 | 3.30E+05 | 1.32E+06 | 6.12 |
| 6 | 2.50E+05 | 3.40E+05 | 2.95E+05 | 1.18E+06 | 6.07 |
| 7 | 8.00E+05 | 7.00E+05 | 7.50E+05 | 3.00E+06 | 6.48 |
| 8 | 6.60E+05 | 4.00E+05 | 5.30E+05 | 2.12E+06 | 6.33 |
| 9 | 2.60E+05 | 2.80E+05 | 2.70E+05 | 1.08E+06 | 6.03 |
| 10 | 2.70E+05 | 2.80E+05 | 2.75E+05 | 1.10E+06 | 6.04 |

The results of Table 1 provide a baseline loading of colony forming units against which the reduction data is compared. As can be seen from Table 1, the average count of colony forming units per mandrel was 1.66E+06 or about 1,660,000, or log 6.22, colony forming units per mandrel. The standard deviation was determined to be log 0.18.

TABLE 2

CFU REDUCTION DUE TO MECHANICAL CONTACT BETWEEN MANDREL AND CARTONS

| Sample # | Time (min) | Result #1 CFU/mL | Result #2 CFU/mL | Average CFU/mL | Average CFU/mandrel | Log/Log Red. (Avg.) |
|---|---|---|---|---|---|---|
| 1 | 0 | 1.65E+05 | 1.27E+05 | 1.46E+05 | 5.84E+05 | 5.77 |
| 2 | 0 | 1.47E+05 | 1.41E+05 | 1.44E+05 | 5.76E+05 | 5.76 |
| 3 | 15 | 1.51E+05 | 1.20E+05 | 1.36E+05 | 5.42E+05 | 5.73 |
| 4 | 15 | 6.80E+04 | 4.90E+04 | 5.85E+04 | 2.34E+05 | 5.37 |
| 5 | 15 | 7.10E+04 | 7.80E+04 | 7.45E+04 | 2.98E+05 | 5.47 |
| 6 | 15 | 6.90E+04 | 7.70E+04 | 7.30E+04 | 2.92E+05 | 5.47/0.23 |
| 7 | 30 | 5.00E+04 | 4.60E+04 | 4.80E+04 | 1.92E+05 | 5.28 |
| 8 | 30 | 6.90E+04 | 7.20E+04 | 7.05E+04 | 2.82E+05 | 5.45 |
| 9 | 30 | 7.90E+04 | 1.01E+05 | 9.00E+04 | 3.60E+05 | 5.56 |
| 10 | 30 | 7.30E+04 | 7.50E+04 | 7.40E+04 | 2.96E+05 | 5.47/0.31 |

Table 2 shows the effect of mechanical contact between the mandrels and the cartons. In the tests conducted, hydrogen peroxide was not applied to the mandrels; rather, the machine was operated at typical operating speed (about 14,000 cartons per hour), and the microbial load (in colony forming units CFU) was measured at times zero, 15 minutes and 30 minutes to determine the microbial load reduction due solely to mechanical contact between the cartons and the mandrels.

The data shown in the columns represent the actual count of colony forming units at the specified times. The average count of colony forming units (in CFU/mandrel) was determined to be: at time zero, 5.8E+05 (log 5.76), with a standard deviation of zero; at time fifteen (15) minutes, 3.24E+05 (log 5.53), with a standard deviation of 0.16 and a log reduction (of the average for this time period, relative to time zero) of 0.23; and at time thirty (30) minutes, 2.83E+05 (log 5.45), with a standard deviation of 0.11 and a log reduction (of the average at this time period, relative to time zero) of 0.31.

In addition, in the column entitled "Log/Log Red. (Avg)", at the end of each non-zero time period (e.g., at the end of the fifteen minute period and the thirty minute period), the log reduction average for that period is shown, as described above.

Figure 5:
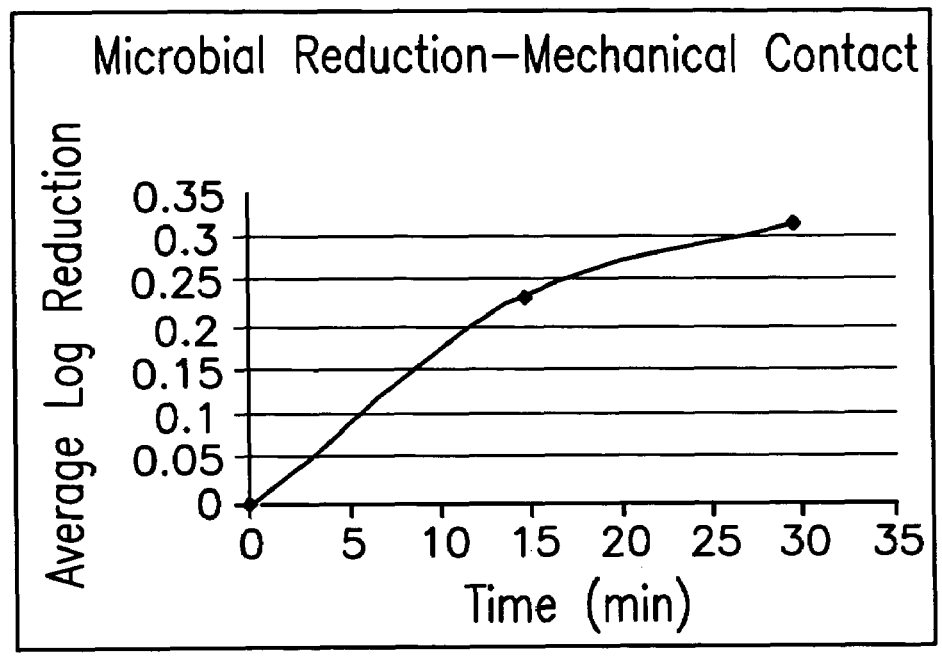
FIG. 5 is a graphical representation of the data of Table 2.

The data of Table 2 shows first that there is a rub-off transfer effect of microbial contamination from the mandrels to the cartons which could effect the microbial reduction data (if not accounted for), but more importantly this data shows that mechanical contact can provide a mechanism for contaminating cartons during actual form, fill and seal operation. The results are shown graphically in FIG. 5.

Referring now to Tables 3A and 3B, below, these tables are compilations of data for evaluating microbial reduction as a function of both time and hydrogen peroxide concentration when vapor is introduced into the bottom heaters. Table 3A represents data for microbial loading at hydrogen peroxide concentrations between zero percent and thirty-five percent at times of zero minutes (start of sterilant introduction) to forty minutes after continuous operation. Table 3B, below, shows the mechanical contact reduction data (in log format) of the data of Table 3A.

TABLE 3A

MICROBIAL (COLONY FORMING UNIT) LOAD PER MANDREL AS A FUNCTION OF TIME AND HYDROGEN PEROXIDE CONCENTRATION DURING NORMAL MACHINE OPERATION

| Time (min.) | Microbial Load (CFU/mandrel) Percent $H_2O_2$ | | | | | |
|---|---|---|---|---|---|---|
| | Zero | 3.12 | 5.77 | 9.55 | 16.76 | 35 |
| 0 | 580000 | 848000 | 566000 | 483000 | 1020667 | 799000 |
| 5 | | | | 71000 | 52967 | 959 |
| 10 | | 187000 | 107000 | 5750 | 1273 | 1 |
| 15 | 341500 | | | | 30 | 1 |
| 20 | | 33400 | 7300 | 106 | 8 | 1 |
| 30 | 282500 | 14100 | 42 | 8 | 4 | |
| 40 | | 2180 | 4 | | | |

Table 3A shows the actual count data of microbial loading per mandrel at times zero minutes (i.e., beginning of process/sterilant introduction), five (5) minutes, ten (10) minutes, fifteen (15) minutes, twenty (20) minutes, thirty (30) minutes and forty (40) minutes of continuous processing, at hydrogen peroxide concentrations from zero (0) percent to thirty-five (35) percent.

TABLE 3B

MICROBIAL (COLONY FORMING UNIT) REDUCTION
IN LOG PER MANDREL AS A FUNCTION OF TIME
AND HYDROGEN PEROXIDE CONCENTRATION
DURING NORMAL MACHINE OPERATION

| Time | Microbial Reduction (Log/mandrel) Percent $H_2O_2$ | | | | | |
|---|---|---|---|---|---|---|
| (min.) | Zero | 3.12 | 5.77 | 9.55 | 16.76 | 35 |
| 0 | 0.00 | 0.00 | 0.00 | 0.00 | 0.00 | 0.00 |
| 5 | | | | 0.83 | 1.22 | 2.92 |
| 10 | | 0.66 | 0.72 | 1.92 | 2.81 | 5.90 |
| 15 | 0.23 | | | | 4.53 | 5.90 |
| 20 | | 1.40 | 1.89 | 3.66 | 5.20 | 5.90 |
| 30 | 0.31 | 1.78 | 4.13 | 4.78 | 5.21 | |
| 40 | | 2.59 | 5.15 | | | |

Figure 6:
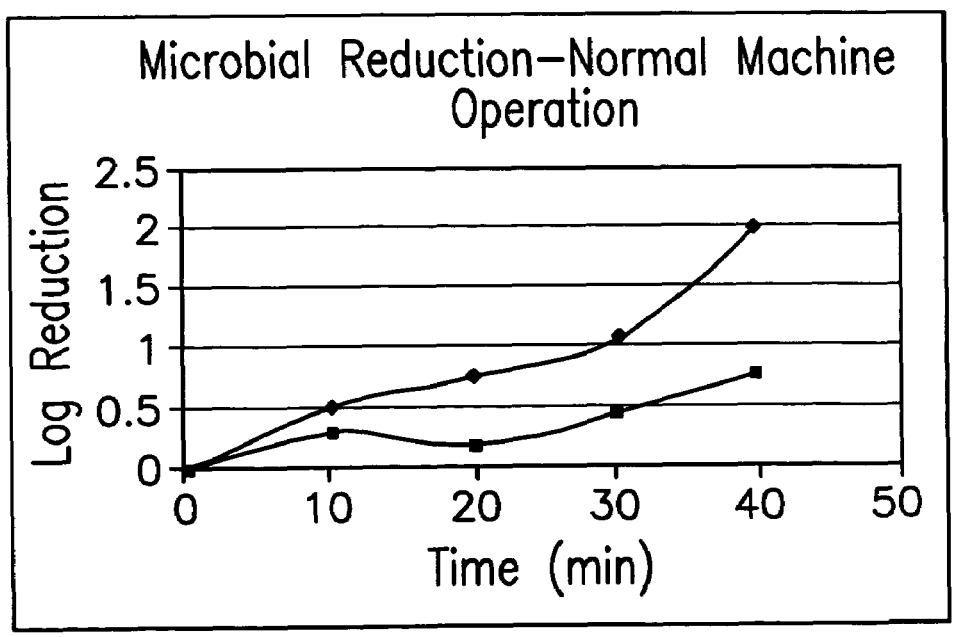
FIG. 6 is a graphical representation of the data of Table 6.
Figure 7:
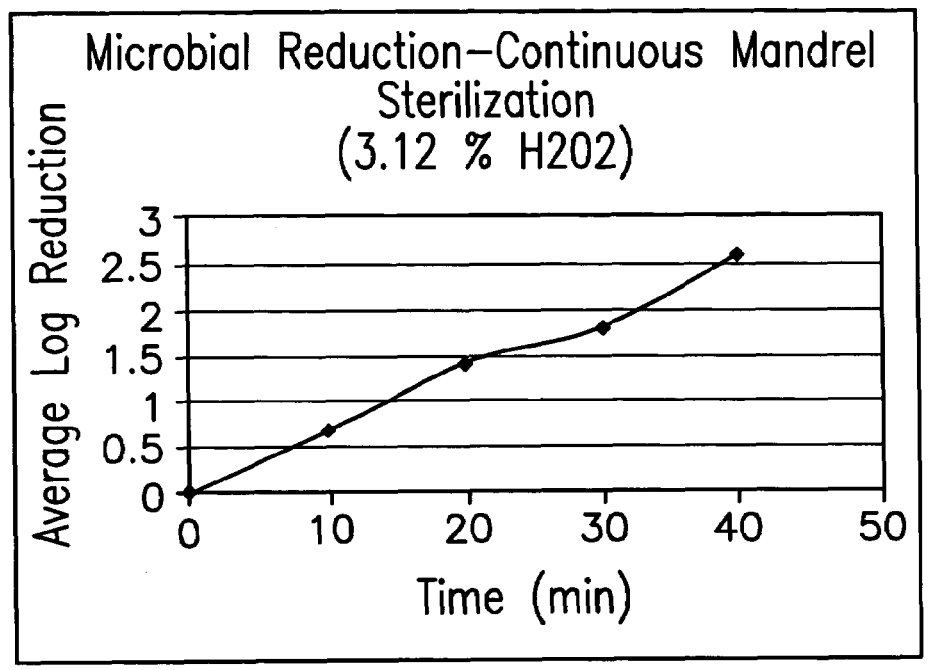
FIG. 7 is a graphical representation of the data of Table 3B for 3.12 percent hydrogen peroxide concentration.
Figure 8:
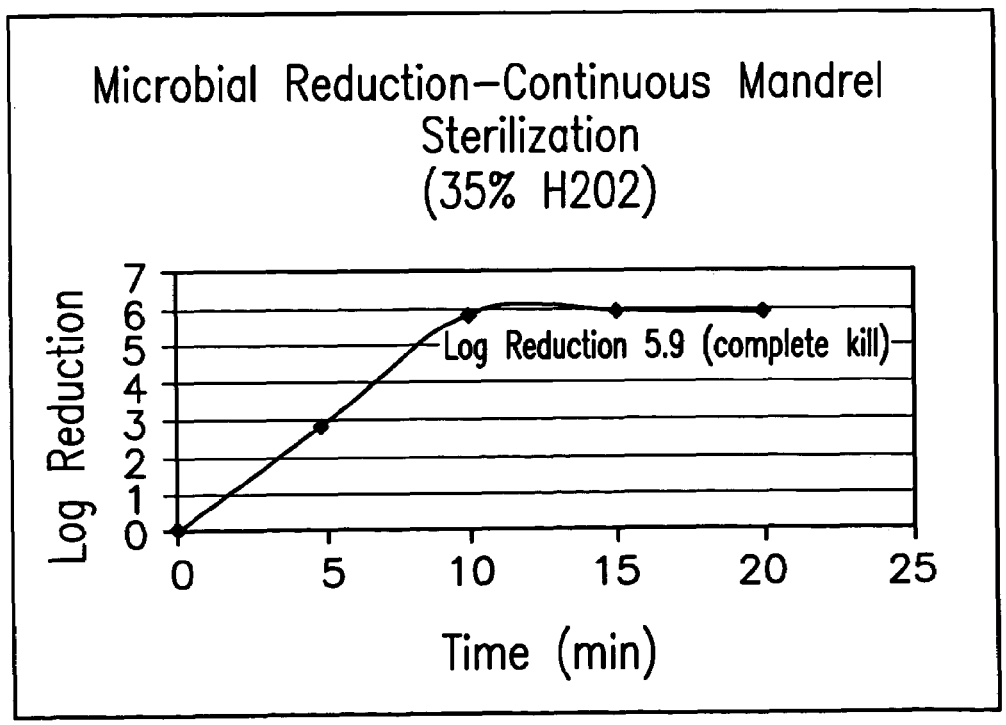
FIG. 8 is a graphical representation of the data of Table 3B for 35 percent hydrogen peroxide concentration.

The data in Table 3B represents the log reduction values (from the raw data of Table 3A). As can be seen, at time zero minutes there was no reduction shown. Microbial reduction was shown as time increased, and as hydrogen peroxide concentration increased. At a hydrogen peroxide concentration of about 3.12 percent, log reductions of 1.78 and 2.59 were seen at times thirty minutes and forty minutes, respectively. As would be expected, increased concentrations of hydrogen peroxide showed very high log reductions (5.20 at twenty minutes at a concentration of about 16.75 percent and complete kill log reduction (5.90) at ten minutes at a concentration of about 35 percent). Thus, the efficacy (i.e., microbial reduction) of the hydrogen peroxide vapor application to the mandrel surface, is well shown. The results as shown in Table 3B are illustrated graphically in FIG. 6 for hydrogen peroxide concentrations of 3.12 percent.

Table 4, below introduces the positive focusing or directing effect exhibited by vapor application when cartons are positioned over the heaters during vapor application. In this part of the analysis, the form, fill and seal machine was operated without cartons and without indexing (rotation) of the mandrels. Essentially, in this part of the analysis, the hydrogen peroxide vapor application was not directed onto the mandrels by the carton. A hydrogen peroxide concentration of 3.12 percent was used for comparison against the data of Table 3.

TABLE 4

MICROBIAL (COLONY FORMING UNIT) REDUCTION
IN LOG PER MANDREL AS A FUNCTION OF TIME
AT CONSTANT PEROXIDE CONCENTRATION AT NO
MACHINE OPERATION AND WITHOUT CARTONS

| Sample # | Time (min) | Result #1 CFU/mL | Result #2 CFU/mL | Average CFU/mL | Average CFU/mandrel | Log/ Log Red. (Avg.) |
|---|---|---|---|---|---|---|
| 1 | 0 | 4.20E+04 | 6.20E+04 | 5.20E+04 | 2.08E+05 | 5.32 |
| 2 | 0 | 1.20E+05 | 1.27E+05 | 1.24E+05 | 4.94E+05 | 5.69 |
| 3 | 15 | 7.80E+04 | 7.90E+04 | 7.85E+04 | 3.14E+05 | 5.50 |
| 4 | 15 | 4.70E+04 | 8.60E+04 | 6.65E+04 | 2.66E+05 | 5.42/0.08 |
| 5 | 30 | 7.40E+04 | 7.40E+04 | 7.40E+04 | 2.96E+05 | 5.47 |
| 6 | 30 | 4.30E+04 | 5.30E+04 | 4.80E+04 | 1.92E+05 | 5.28 |
| 7 | 30 | 7.80E+04 | 7.50E+04 | 7.65E+04 | 3.06E+05 | 5.49 |
| 8 | 30 | 7.80E+04 | 6.90E+04 | 7.35E+04 | 2.94E+05 | 5.47/0.11 |

The data shown in the columns represent the actual count of colony forming units at the specified times. The average count of colony forming (CFU/mandrel) units was determined to be: at time zero, 3.51E+05 (log 5.55), with a standard deviation of 0.27; at time fifteen (15) minutes, 2.90E+05 (log 5.46), with a standard deviation of 0.05 and a log reduction (of the average for this time period, relative to time zero) of 0.08; and at time thirty (30) minutes, 2.72E+05 (log 5.43), with a standard deviation of 0.10 and a log reduction (of the average at this time period, relative to time zero) of 0.11.

As seen by the data of Table 4 in comparison to that of the data in Table 3B for the same hydrogen peroxide concentration and at the same times, it is readily seen that there is a significant improvement in log reduction when the machine is operated in a normal mode, that is with cartons running the machine, compared to application without cartons running. This further show and supports the efficacy of applying the sterilant onto the mandrel surfaces. Moreover, as will be recognized by those skilled in the art, this data supports use of fixed (e.g., mechanical) guides to direct the sterilant gas onto the mandrel surface even when cartons are not present. Thus, the use of the present system, to provide for sterilizing these (and other) carton forming surfaces during machine start up and prior to production is accorded.

Table 5, below is a compilation of data of the actual count of colony forming units taken with the form, fill and seal packaging machine operating at low speed, with the mandrels being indexed, and operating without cartons. This is a procedure similar to that used to develop the data of Table 4, with the machine indexed at a slower speed, and at a constant hydrogen peroxide concentration (concentration of 2.59 percent). The data was collected by taking swab samples at the mandrel cap 35 (represented by C in the Table) and on the mandrel side tubes 37 (represented by T in the Table).

TABLE 5

MICROBIAL (COLONY FORMING UNIT) REDUCTION IN LOG
PER MANDREL AS A FUNCTION OF TIME AT CONSTANT PEROXIDE
CONCENTRATION AT MACHINE OPERATION AT SLOW SPEED
WITHOUT CARTONS AND AT VARYING SWAB SITES

| Sample # | Time (min) | Swab Site | Result 1 CFU/mL | Result #2 CFU/mL | Average CFU/mL | Average CFU/mandrel | Log/Log Red. (Avg) |
|---|---|---|---|---|---|---|---|
| 1 | 0 | C | 1.19E+05 | 1.26E+05 | 1.23E+05 | 4.90E+05 | 5.69 |
| 2 | 0 | T | 2.36E+05 | 2.09E+05 | 2.23E+05 | 8.90E+05 | 5.95 |

TABLE 5-continued

MICROBIAL (COLONY FORMING UNIT) REDUCTION IN LOG
PER MANDREL AS A FUNCTION OF TIME AT CONSTANT PEROXIDE
CONCENTRATION AT MACHINE OPERATION AT SLOW SPEED
WITHOUT CARTONS AND AT VARYING SWAB SITES

| Sample # | Time (min) | Swab Site | Result 1 CFU/mL | Result #2 CFU/mL | Average CFU/mL | Average CFU/mandrel | Log/Log Red. (Avg) |
|---|---|---|---|---|---|---|---|
| 3 | 0 | C | 1.24E+05 | 1.13E+05 | 1.19E+05 | 4.74E+05 | 5.68 |
| 4 | 0 | T | 1.05E+05 | 1.17E+05 | 1.11E+05 | 4.44E+05 | 5.65 |
| 5 | 15 | C | 6.80E+04 | 6.30E+04 | 6.55E+04 | 2.62E+05 | 5.42 |
| 6 | 15 | T | 1.03E+05 | 9.90E+04 | 1.01E+05 | 4.04E+05 | 5.61 |
| 7 | 15 | C | 1.16E+05 | 1.00E+05 | 1.08E+05 | 4.32E+05 | 5.64/0.14 |
| 8 | 15 | T | 1.06E+05 | 9.40E+04 | 1.00E+05 | 4.00E+05 | 5.60/0.22 |
| 9 | 30 | C | 6.50E+04 | 6.80E+04 | 6.65E+04 | 2.66E+05 | 5.42 |
| 10 | 30 | T | 1.22E+05 | 1.15E+05 | 1.19E+05 | 4.74E+05 | 5.68 |
| 11 | 30 | C | 1.49E+05 | 1.00E+05 | 1.25E+05 | 4.98E+05 | 5.70/0.10 |
| 12 | 30 | T | 8.90E+04 | 1.08E+05 | 9.85E+04 | 3.94E+05 | 5.60/0.19 |
| 13 | 45 | C | 1.51E+05 | 1.35E+05 | 1.43E+05 | 5.72E+05 | 5.76 |
| 14 | 45 | T | 1.67E+05 | 1.34E+05 | 1.51E+05 | 6.02E+05 | 5.78 |
| 15 | 45 | C | 1.64E+05 | 1.81E+05 | 1.73E+05 | 6.90E+05 | 5.84/−0.12 |
| 16 | 45 | T | 2.49E+05 | 2.54E+05 | 2.52E+05 | 1.01E+06 | 6.00/−0.08 |
| 17 | 60 | C | 6.30E+04 | 8.40E+04 | 7.35E+04 | 2.94E+05 | 5.47 |
| 18 | 60 | T | 2.10E+05 | 1.63E+05 | 1.87E+05 | 7.46E+05 | 5.87 |
| 19 | 60 | C | 8.50E+04 | 9.20E+04 | 8.85E+04 | 3.54E+05 | 5.55/0.17 |
| 20 | 60 | T | 1.20E+05 | 1.08E+05 | 1.14E+05 | 4.56E+05 | 5.66/0.05 |

In Table 5, the data shown in the columns represent the actual count of colony forming units at the specified times. The average count of colony forming (CFU/mandrel) units was determined to be: at time zero at the cap 4.82E+05 (log 5.68), with a standard deviation of 0.01, and at the side tubes 6.67E+05 (log 5.82), with a standard deviation of 0.21; at time fifteen (15) minutes at the cap 3.47E+05 (log 5.54), with a standard deviation of 0.15 and a log reduction (of the average for this time period, relative to time zero) of 0.14, and at the side tubes 4.02E+05 (log 5.60), with a standard deviation of 0.0 and a log reduction (of the average for this time period, relative to time zero) of 0.22; at time thirty (30) minutes at the cap, 3.82E+05 (log 5.58), with a standard deviation of 0.19 and a log reduction (of the average at this time period, relative to time zero) of 0.10, and at the side tubes 4.34E+05 (log 5.64), with a standard deviation of 0.06 and a log reduction (of the average for this time period, relative to time zero) of 0.19; at time forty-five (45) minutes at the cap, 6.31E+05 (log 5.80), with a standard deviation of 0.06 and a log reduction (of the average at this time period, relative to time zero) of −0.12, and at the side tubes 8.04E+05 (log 5.91), with a standard deviation of 0.16 and a log reduction (of the average for this time period, relative to time zero) of −0.08; and at sixty (60) minutes at the cap, 3.24E+05 (log 5.51), with a standard deviation of 0.06 and a log reduction (of the average at this time period, relative to time zero) of 0.17, and at the side tubes 6.01E+05 (log 5.78), with a standard deviation of 0.15 and a log reduction (of the average for this time period, relative to time zero) of 0.05.

The data of Table 5 (when compared to that of Table 3B) again shows the increased microbial reduction when operating with cartons in place on the form, fill and seal packaging machine. The mandrel side tube data is the sum of all of the side tubes.

Table 6 below is a test similar to that for which data is represented in Table 5, except that the form, fill and seal packaging machine was operated with cartons in place, at a constant hydrogen peroxide concentration (concentration of 2.52 percent). The data was collected by taking swab samples at the mandrel cap (C) and on the mandrel side tubes (T). The mandrel side tube data is the sum of all of the side tubes.

TABLE 6

MICROBIAL (COLONY FORMING UNIT) REDUCTION IN
LOG PER MANDREL AS A FUNCTION OF TIME AT
CONSTANT PEROXIDE CONCENTRATION AT NORMAL
OPERATING SPEED WITH CARTONS AND AT VARYING
SWAB SITES

| Sample # | Time (min) | Swab Site | Result #1 CFU/mL | Result #2 CFU/mL | Average CFU/mL | Average CFU/mandrel | Log/Log Red. (Avg) |
|---|---|---|---|---|---|---|---|
| 1 | 0 | C | 1.19E+05 | 1.45E+05 | 1.32E+05 | 5.28E+05 | 5.72 |
| 2 | 0 | T | 1.39E+05 | 2.27E+05 | 1.83E+05 | 7.32E+05 | 5.86 |
| 3 | 0 | C | 1.30E+05 | 1.15E+05 | 1.23E+05 | 4.90E+05 | 5.69 |
| 4 | 0 | T | 1.71E+05 | 1.75E+05 | 1.73E+05 | 6.92E+05 | 5.84 |
| 5 | 10 | C | 3.50E+04 | 3.20E+04 | 3.35E+04 | 1.34E+05 | 5.13 |
| 6 | 10 | T | 8.80E+04 | 9.70E+04 | 9.25E+04 | 3.70E+05 | 5.57 |
| 7 | 10 | C | 4.40E+04 | 4.60E+04 | 4.50E+04 | 1.80E+05 | 5.26/0.51 |
| 8 | 10 | T | 1.06E+05 | 6.70E+04 | 8.65E+04 | 3.46E+05 | 5.54/0.30 |
| 9 | 20 | C | 1.93E+04 | 1.86E+04 | 9.00E+04 | 3.60E+05 | 4.88 |
| 10 | 20 | T | 1.24E+05 | 1.55E+05 | 1.40E+05 | 5.58E+05 | 5.75 |

TABLE 6-continued

MICROBIAL (COLONY FORMING UNIT) REDUCTION IN
LOG PER MANDREL AS A FUNCTION OF TIME AT
CONSTANT PEROXIDE CONCENTRATION AT NORMAL
OPERATING SPEED WITH CARTONS AND AT VARYING
SWAB SITES

| Sample # | Time (min) | Swab Site | Result #1 CFU/mL | Result #2 CFU/mL | Average CFU/mL | Average CFU/mandrel | Log/Log Red. (Avg) |
|---|---|---|---|---|---|---|---|
| 11 | 20 | C | 2.82E+04 | 2.25E+04 | 2.54E+04 | 1.01E+05 | 5.01/0.76 |
| 12 | 20 | T | 9.20E+04 | 7.80E+04 | 8.50E+04 | 3.40E+05 | 5.53/0.20 |
| 13 | 30 | C | 1.41E+04 | 1.12E+04 | 1.27E+04 | 5.06E+04 | 4.70 |
| 14 | 30 | T | 6.30E+04 | 6.20E+04 | 6.25E+04 | 2.50E+05 | 5.40 |
| 15 | 30 | C | 8.20E+03 | 1.04E+04 | 9.30E+03 | 3.72E+04 | 4.57/1.06 |
| 16 | 30 | T | 5.10E+04 | 7.30E+04 | 6.20E+04 | 2.48E+05 | 5.39/0.46 |
| 17 | 40 | C | 9.30E+02 | 7.80E+02 | 8.55E+02 | 3.42E+03 | 3.53 |
| 18 | 40 | T | 2.50E+04 | 2.92E+04 | 2.71E+04 | 1.08E+05 | 5.04 |
| 19 | 40 | C | 1.89E+03 | 1.61E+03 | 1.75E+03 | 7.00E+03 | 3.85/1.99 |
| 20 | 40 | T | 2.89E+04 | 3.21E+04 | 3.05E+04 | 1.22E+05 | 5.09/0.79 |

In Table 6, the data shown in the columns represent the actual count of colony forming units at the specified times. The average count of colony forming (CFU/mandrel) units was determined to be: at time zero at the cap 5.09E+05 (log 5.71), with a standard deviation of 0.02, and at the side tubes 7.12E+05 (log 5.85), with a standard deviation of 0.02; at time ten (10) minutes at the cap 1.57E+05 (log 5.20), with a standard deviation of 0.09 and a log reduction (of the average for this time period, relative to time zero) of 0.51, and at the side tubes 3.58E+05 (log 5.55), with a standard deviation of 0.02 and a log reduction (of the average for this time period, relative to time zero) of 0.30; at time twenty (20) minutes at the cap, 8.86E+04 (log 4.95), with a standard deviation of 0.09 and a log reduction (of the average at this time period, relative to time zero) of 0.76, and at the side tubes 4.49E+05 (log 5.65), with a standard deviation of 0.15 and a log reduction (of the average for this time period, relative to time zero) of 0.20; at time thirty (30) minutes at the cap, 4.39E+04 (log 4.64), with a standard deviation of 0.09 and a log reduction (of the average at this time period, relative to time zero) of 1.06, and at the side tubes 2.49E+05 (log 5.40), with a standard deviation of 0.0 and a log reduction (of the average for this time period, relative to time zero) of 0.46; and at forty (40) minutes at the cap, 5.21E+03 (log 3.72), with a standard deviation of 0.22 and a log reduction (of the average at this time period, relative to time zero) of 1.99, and at the side tubes 1.15E+05 (log 5.06), with a standard deviation of 0.04 and a log reduction (of the average for this time period, relative to time zero) of 0.79.

Again, the data of Table 6 shows the significant microbial reduction at the mandrel (and in particular at the mandrel cap) when operating the form, fill and seal packaging machine using the automatic, continuous sterilization system of the present invention. These data are shown graphically in FIG. 6, in which the data for the mandrel caps is indicated by the filled diamonds and the data for the mandrel tubes is indicated by the filled squares. Specifically, the data of Table 6 shows that an average log reductions at the mandrel caps of 1.06 and 1.99 can be achieved with the machine operating after 30 minutes and 40 minutes respectively. Product spoilage studies have shown that this microbial reduction can provide a higher level of assurance vis-a-vis extended product shelf life and can further provide benefits with respect to reducing the number of packages rejected due to spoilage during the intended shelf life of the product.

It will be appreciated by those skilled in the art that the present system, which provides automatic continuous sterilization of product container contact surfaces by application of sterilant to these surfaces will facilitate the reduction of build up of contamination and continuously sterilizes these surfaces to prevent any contaminated particles from reaching these surfaces.

It will also be appreciated by those skilled in the art that additional shields and guards can be added to the carton heater 40 to direct sterilant to the mandrel 34 surfaces in a manner similar to that effected by the cartons. As such, the mandrels 34 will be sterilized in a like process to that demonstrated when cartons are present.

All patents referred to herein, are hereby incorporated herein by reference, whether or not specifically do so within the text of this disclosure.

In the present disclosure, the words "a" or "an" are to be taken to include both the singular and the plural. Conversely, any reference to plural items shall, where appropriate, include the singular.

From the foregoing it will be observed that numerous modification and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An automatic, continuous sterilization system for a form, fill and seal packaging machine, the form, fill and seal packaging machine for forming, filling and sealing packages, the machine having a turret carrying a plurality of mandrels on which the packages are carried, the packages being positioned with the mandrels inside of the packages, the machine farther having a bottom panel heating station having a reciprocating bottom panel heater, the sterilization system comprising:

a sterilant source for supplying a sterilant;
a sterilant inlet at the bottom panel heater; and
a nozzle at the sterilant inlet for introducing sterilant to the bottom panel heater wherein the nozzle is mounted at the bottom panel heating,
wherein packages are positioned on one of the plurality of mandrels and are indexed to the bottom panel heater, and
wherein the sterilant is introduced to the mandrel at the bottom panel heating station when the carton is positioned on the mandrel, introduction of the sterilant providing a log reduction of microbial colony forming units of at least 1.4 after twenty minutes of machine operation with a sterilant concentration of less than about 3.12 percent, and wherein a surface temperature of the mandrels is maintained at a temperature that precludes condensation on the mandrels.

2. The sterilization system in accordance with claim 1 including a sterilant vaporizer, and wherein the sterilant is vaporized prior to inlet at the bottom panel heater.

3. The sterilization system in accordance with claim 2 wherein the sterilant is vaporized hydrogen peroxide.

4. The sterilization system in accordance with claim 3 wherein the hydrogen peroxide concentration is less than about 50 percent.

5. The sterilization system in accordance with claim 4 wherein the hydrogen peroxide concentration is about 3 percent.

6. The sterilization system in accordance with claim 1 wherein the sterilant source is a common source for the form, fill and seal packaging machine.

7. An automatic, continuous sterilization system for a form, fill and seal packaging machine, the form, fill and seal packaging machine for forming, filling and sealing packages, the machine having a turret carrying a plurality of mandrels on which the packages are carried, the packages being positioned with the mandrels inside of the packages, the machine farther having a bottom panel heating station having a reciprocating bottom panel heater, the sterilization system comprising:

a sterilant source for supplying a sterilant; and means at the bottom panel heater for introducing a sterilant to a selected one of the mandrels at the bottom panel heater when a package is positioned on one of the plurality of mandrels and is indexed to the bottom panel heater; wherein the means is mounted at the bottom panel and means for precluding sterilant condensation on the mandrels.

8. The sterilization system in accordance with claim 7 including a vapor generating system for vaporizing the sterilant, wherein the sterilant is vaporized prior to introduction to the bottom panel heater.

\* \* \* \* \*